United States Patent [19]
Arnold

[11] Patent Number: 6,011,027
[45] Date of Patent: Jan. 4, 2000

[54] USE OF 19-NOR-4-ANDROSTENEDIOL TO INCREASE 19-NORTESTOSTERONE LEVELS IN HUMANS

[75] Inventor: Patrick Arnold, Seymour, Ill.

[73] Assignee: LPJ Research, Inc., Seymour, Ill.

[21] Appl. No.: 09/252,166

[22] Filed: Feb. 18, 1999

[51] Int. Cl.$^7$ ..................................................... A61K 31/56
[52] U.S. Cl. ............................................................. 514/182
[58] Field of Search ............................................... 514/182

[56] References Cited

U.S. PATENT DOCUMENTS 2,843,608  7/1958  Colton .
3,862,195  1/1975  Gastaud .
4,083,973  4/1978  van der Vies .
5,342,834  8/1994  Bardin et al. .

OTHER PUBLICATIONS

Merck Index, Entry 1325, 1989.

*Primary Examiner*—Rebecca Cook
*Attorney, Agent, or Firm*—Michael Berns; Berns Law Office, PC

[57] ABSTRACT

This invention involves the administration of the 19-nortestosterone precursor 19-nor-4-androstenediol as a means of increasing 19-nortestosterone levels in humans.

5 Claims, No Drawings

USE OF 19-NOR-4-ANDROSTENEDIOL TO INCREASE 19-NORTESTOSTERONE LEVELS IN HUMANS

FIELD OF THE INVENTION

This invention involves the administration of the 19-nortestosterone precursor 19-nor-4-androstenediol as a means of increasing 19-nortestosterone levels in humans.

DESCRIPTION OF THE PRIOR ART 19-nortestosterone is a naturally occurring compound in the body, similar to testosterone, which provides positive benefits to the body. Prior methods of increasing nortestosterone levels have been by the administration of nortestosterone derivatives. U.S. Pat. No. 3,862,195 to Gastaud describes administration of compounds of 19-nortestosterone having anabolic or androgenic activity. U.S. Pat. No. 4,083,973 to van der Vies describes the use of 17.beta.-ester of nandrolone. U.S. Pat. No. 5,342,834 to Bardin and Monder describes a method of androgen supplementation utilizing compounds such as 7.alpha.-methyl-19-nortestosterone. U.S. patent application Ser. No. 09/114,114, also by Patrick Arnold, discloses a method of effectively increasing testosterone levels in humans by the oral administration of the testosterone precursor 4-androstenediol. The present invention increases levels of nortestosterone in the body by administration of precursors.

DESCRIPTION OF THE INVENTION

The steroid hormone testosterone is considered to be the male virilizing hormone. Its effects include maintenance of muscle and bone mass, sexual function, and psychological well being among others. As males grow older, especially after the age of 35, a slow decline in testosterone levels is observed which is accompanied by symptoms that have been associated with the condition known as "andropause". Symptoms of andropause include lethargy, depression, lack of sexual desire and function, and loss of muscle mass and strength.

The steroid hormone 19-nortestosterone is a close chemical derivative of testosterone. Chemically speaking it is testosterone without the axial methyl group (C19) stemming off of C10. Testosterone's effects on maintenance of muscle and bone mass are termed anabolic effects, while its effects on the development and maintenance and of male sexual organs and male virilization effects (facial hair growth, body hair growth, male pattern baldness, lowering of voice pitch etc.) are termed androgenic effects. 19- nortestosterone differs from testosterone in its therapeutic activity because although it has approximately the same anabolic activity of testosterone, it is significantly less androgenic. This property makes it valuable to those wishing to increase lean body mass, combat osteoporosis, and increase energy levels while avoiding androgenic effects. Examples of persons that would want to avoid androgenic effects would be women, and men with prostate and/or male pattern baldness problems.

There are several pharmaceutical methods to increase nortestosterone levels in humans to therapeutically effective levels. Many of these have certain disadvantages however. Nortestosterone esters in oil depot form (i.e. nandrolone decanoate) have been used as injections for decades, however these injections can be inconvenient and often painful. These depot injections also result in inconsistent blood levels as a supraphysiological surge is seen soon after injection but by the time the next injection is due the levels have often dropped down below therapeutically effective levels. This is in contrast with male sex hormone levels under normal conditions, which are quite stable within mild release pulses of approximately 90 minutes duration. Supraphysiological surges that are seen with injectable preparations may increase the incidence of undesirable side effects such as amplified shutdown of the hypothalamic/pituitary testicular axis (HPTA).

Other pharmaceutical methods for norandrogen therapy include oral nortestosterone derivatives. These compounds (i.e. norethandrolone and ethylestrenol) are altered in the 17alpha position of the steroid molecule with an alkyl group. This alkyl group renders the steroid impervious to oxidation of the 17beta-hydroxyl group in the liver and therefore greatly improves its oral bioavailablity compared to the non-alkylated steroids. However this structural modification also has been associated with a greatly increased risk of hepatotoxicity. Therefore these synthetic compounds are far from an ideal solution.

U.S. patent application Ser. No. 09/114,114, also by Patrick Arnold, discloses a method of effectively increasing testosterone levels in humans by the oral administration of the testosterone precursor 4-androstenediol. The pharmacokinetics of the administration of this precursor is such that a peak in blood levels is seen at approximately 90 minutes with a subsequent decline to baseline within 3 hours. This fact permits one to more closely simulate the natural endogenous pulsatile release of testosterone through multiple daily dosing of 4-androstenediol. This should result in a more normal physiological response with a minimization of side effects and HPTA shutdown. Furthermore, since 4-androstenediol is not a 17alpha alkylated compounds, its hepatotoxicity is minimal.

It was the intention of the researchers to show that the advantages of 4-androstenediol as a testosterone elevating agent can also be achieved with its 19-nor analog (19-nor-4-androstenediol) as a 19-nortestosterone elevating agent.

19-nor-4-androstenediol is the 19-nor analog of 4-androstenediol. 19-norandrogens are considered to share essentially the same metabolic pathways as C19-androgens (Engell L L, Alexander J,.1: Bio. Chem., 1958, 231, 159–65). Therefore it was the hope of the researchers that 19-nor-4-androstenediol would convert effectively to 19-nortestosterone via the 3beta-hydroxysteroid dehydrogenase enzyme.

In an effort to prove this theory a clinical study was therefore undertaken by the inventor. Specifically it was the intention of the inventor to investigate whether 19-nor-4-androstenediol would act as an effective in-vivo peroral 19-nortestosterone precursor in man.

The chemical term 19-nor-4-androstenediol refers to two isomers; 19-nor-4-androstene-3beta, 17beta-diol and 19-nor-4-androstene-3alpha, 17beta-diol. This invention concerns primarily the former (and more predominant) isomer.

Oral 19-nor-4-androstenediol can be given in daily doses of 25 mg. to 1000 mg.; preferably 100 to 500 mg. These daily doses can be divided into several subdoses with 3–5 being most preferable. In addition to peroral administration, 19-nor-4-androstenediol can also be effectively administered by several other routes including transdermal, rectal (suppository), intranasal, and sublingual. A particular advantageous method of sublingual administration involves complexing 19-nor-4-androstenediol with beta-hydroxypropyl-beta-cyclodextrin, which is then pressed into tablets.

I claim:

1. A method of increasing the 19-nortestosterone level in an individual, said method comprising administering to said individual an effective amount of 19-nor-4-androstenediol.

2. The method of claim 1 wherein said administration is peroral.

3. The method of claim 1 wherein said administration is selected from the group consisting of transdermal, rectal, intranasal, and sublingual.

4. The method of claim 1, wherein said amount is a daily dosage of 25 to 1000 mg.

5. The method of claim 1 wherein said 19-nor-4-androstenediol is 19-nor-4-androstene-3beta, 17beta-diol.

* * * * *